United States Patent [19]

Dumoulin et al.

[11] Patent Number: 5,318,025
[45] Date of Patent: Jun. 7, 1994

[54] TRACKING SYSTEM TO MONITOR THE POSITION AND ORIENTATION OF A DEVICE USING MULTIPLEXED MAGNETIC RESONANCE DETECTION

[75] Inventors: Charles L. Dumoulin, Ballston Lake, N.Y.; Steven P. Souza, Williamstown, Mass.; Robert D. Darrow, Scotia, N.Y.

[73] Assignee: General Electric Company, Schenectady, N.Y.

[21] Appl. No.: 861,690

[22] Filed: Apr. 1, 1992

[51] Int. Cl.⁵ ............................................. A61B 5/055
[52] U.S. Cl. ...................... 128/653.200; 128/653.500; 128/658; 128/899
[58] Field of Search .................. 128/653.2, 653.5, 899, 128/658

[56] References Cited

U.S. PATENT DOCUMENTS

| | | | |
|---|---|---|---|
| 3,799,015 | 1/1989 | Sepponen | 128/653.002 |
| 4,254,778 | 3/1981 | Clow et al. | 128/653.002 |
| 4,572,198 | 2/1986 | Codrington | 128/653.002 |
| 4,613,837 | 9/1986 | Blass et al. | 128/653.005 |
| 4,638,252 | 1/1987 | Bradshaw | 128/653.005 |
| 4,672,972 | 6/1987 | Berke | 128/653.005 |
| 4,889,127 | 12/1989 | Takeda et al. | 128/653.002 |
| 4,962,763 | 10/1990 | Sato et al. | 128/653.002 |
| 4,966,149 | 10/1990 | Stokar | 128/653.002 |
| 4,989,608 | 2/1991 | Ratner | 128/653.002 |
| 4,995,394 | 2/1991 | Cline et al. | 128/653.002 |
| 5,005,592 | 4/1991 | Cartmell | 128/899 |
| 5,042,486 | 8/1991 | Pfeiler et al. | 128/653.001 |
| 5,099,845 | 3/1992 | Besz et al. | 128/899 |
| 5,107,862 | 4/1992 | Fabian et al. | 128/899 |
| 5,170,789 | 12/1992 | Narayan et al. | 128/653.5 |

FOREIGN PATENT DOCUMENTS 0385367 9/1990 European Pat. Off. .
3937052 5/1990 Fed. Rep. of Germany .

Primary Examiner—Lee S. Cohen
Assistant Examiner—Brian L. Casler
Attorney, Agent, or Firm—Lawrence P. Zale; Marvin Snyder

[57] ABSTRACT

A tracking system employs magnetic resonance signals to monitor the position and orientation of at least one device such as a catheter within a subject. The device has a plurality of receiver coils which are sensitive to magnetic resonance signals generated in the subject. These signals are detected in the presence of magnetic field gradients and thus have frequencies which are substantially proportional to the location of the coil along the direction of the applied gradient. Signals are detected responsive to sequentially applied mutually orthogonal magnetic gradients to determine the device's position and orientation in several dimensions. The position and orientation of the device as determined by the tracking system is superimposed upon independently acquired medical diagnostic images. One or more devices can be simultaneously tracked.

16 Claims, 6 Drawing Sheets

TRACKING SYSTEM TO MONITOR THE POSITION AND ORIENTATION OF A DEVICE USING MULTIPLEXED MAGNETIC RESONANCE DETECTION

CROSS REFERENCES TO RELATED APPLICATIONS

This application is related to U.S. Patent applications TRACKING SYSTEM TO MONITOR THE POSITION AND ORIENTATION OF A DEVICE USING MAGNETIC RESONANCE DETECTION OF A SAMPLE CONTAINED WITHIN THE DEVICE, Ser. No. 07/861,662 filed Apr. 1, 1992 and TRACKING SYSTEM AND PULSE SEQUENCES TO MONITOR THE POSITION AND ORIENTATION OF A DEVICE USING MAGNETIC RESONANCE, Ser. No. 07/861,718 filed Apr 1, 1992 by Dr. Charles L. Dumoulin, Dr. Steven P. Souza and Robert Darrow all assigned to the present assignee, hereby incorporated by reference, and filed simultaneously with this application.

BACKGROUND OF THE INVENTION

1. Field of the Invention

The present invention relates to medical procedures in which a device is inserted into a body, and more particularly concerns tracking of such device with the use of magnetic resonance signals.

2. Description of Related Art

X-ray fluoroscopes are used routinely to monitor placement of devices during diagnostic and therapeutic medical procedures. Conventional X-ray fluoroscopes are designed to minimize X-ray dosage. Nevertheless, some procedures can be very long and the accumulated X-ray dose to the subject can become significant. The long term exposure of the attending medical staff is of even greater concern since they participate in these procedures regularly. Consequently, it is desirable to reduce or eliminate the X-ray dose during these procedures.

Another limitation on the use of X-ray fluoroscopes is that the technique is projective in nature and produces a single two-dimensional image. Information concerning the depth of an object within the field-of-view is not available to the operator. It is often desirable to obtain this information during surgical procedures.

Several method of using rf signals to track a device in the body have been disclosed in U.S. Patent Applications TRACKING SYSTEM TO MONITOR THE POSITION AND ORIENTATION OF A DEVICE WITH RADIOFREQUENCY FIELD GRADIENTS Ser. No. 07/753,565 by C. Dumoulin, R. Darrow, J. Schenck and S. Souza; TRACKING SYSTEM TO MONITOR THE POSITION AND ORIENTATION OF A DEVICE WITH RADIOFREQUENCY FIELDS Ser. No. 07/753,563 by C. Dumoulin, R. Darrow, J. Schenck and P. Roemer; STEREOSCOPIC X-RAY FLUOROSCOPY SYSTEM USING RADIO FREQUENCY FIELDS by C. Dumoulin and R. Darrow; AUTOMATIC GANTRY POSITIONING FOR IMAGING SYSTEMS Ser. No. 07/753,567 by C. Dumoulin and R. Darrow; and MULTI-PLANAR X-RAY FLUOROSCOPY SYSTEM USING RADIOFREQUENCY FIELDS Ser. No. 07/753,566 by R. Darrow and C. Dumoulin all filed on Sep. 3, 1991. These method do not require the use of X-rays but employs rf transmitting and receiving apparatus to track a device in a body.

Currently, there is a need for a simple method of tracking a device in an imaging system which requires little modification to the existing system and does not require X-ray radiation for tracking.

SUMMARY OF THE INVENTION

Tracking of catheters and other devices being positioned within a body, without using X-rays, is accomplished by using a magnetic resonance (MR) imaging system comprised of a magnet, pulsed magnetic field gradient system, a radio-frequency transmitter, a radio-frequency receiver and a controller. A device to be tracked is modified by attaching a plurality of small radiofrequency (rf) coils to it. A subject is placed in the magnet bore and the device is introduced into the subject. The MR system generates a series of rf and magnetic field gradient pulses transmitted into the subject which induce a resonant MR response signal from selected nuclear spins within the subject. The MR response signal induces current in the rf coils attached to the device. Since the rf coils are small, their region of sensitivity is liraited. Consequently, only nuclear spins in the immediate vicinity of each rf coil are detected by that respective rf coil. The MR response signal is propagated to a low-noise preamplifier where each is amplified, and thence to the transmitter from which they are emitted. A receiver system receives the signals detected from each of the rf coils and demodulates, amplifies, filters and digitizes each of the signals which are then stored as data by a controller. Data are acquired during the sequential application of magnetic field gradients in three orthogonal directions. These gradients cause the frequency of the detected signal to be directly proportional to the position of each rf coil along each applied gradient. The digitized data are then processed using Fourier transformations to calculate the position of each rf coil in three dimensions. The positions of all rf coils can be used to determine the location and orientation of the device. This positional information can then be superimposed on an NM image of the region of interest. Simultaneous reception by multiple coils can be accomplished using either time or frequency multiplexing schemes.

OBJECTS OF THE INVENTION

It is an object of the present invention to provide a system for tracking both orientation and location of at least one device within a body without using X-rays.

It is another object of the present invention to provide a method of tracking both orientation and location of at least one device in a living body during an MR examination.

It is another object of the present invention to provide an interactive image providing both location and orientation information for at least one device superimposed upon another image.

It is another object of the present invention to provide location information for a plurality of devices within a body by using time multiplexing.

It is another object of the present invention to provide location information for a plurality of devices within a body by using frequency multiplexing.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

DETAILED DESCRIPTION OF THE INVENTION

Figure 1:
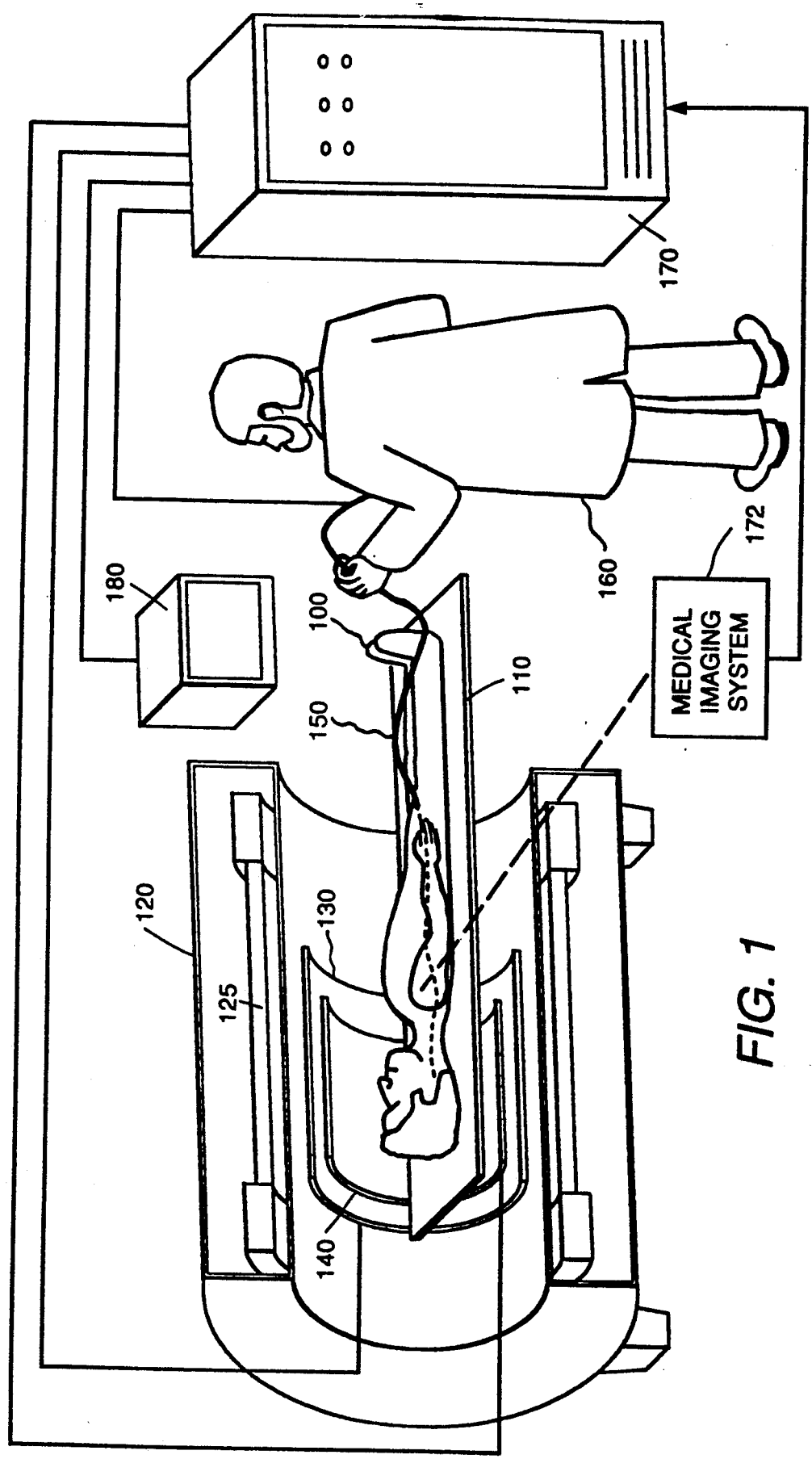
FIG. 1 is a perspective view of one embodiment of the present invention in operation tracking the location of a device in a subject.

In FIG. 1, a subject 100 on a support table 110 is placed in a homogeneous magnetic field generated by a magnet 125 in magnet housing 120. Magnet 125 and magnet housing 120 have cylindrical symmetry and is shown sectioned in half to reveal the position of subject 100. A region of subject 100 into which a device 150, shown as a catheter, is inserted, is located in the approximate center of the bore of magnet 125. Subject 100 is surrounded by a set of cylindrical magnetic field gradient coils 130 which create magnetic field gradients of predetermined strength at predetermined times. Gradient coils 130 generate magnetic field gradients in three mutually orthogonal directions. A plurality of external coils 140 (only one is shown in FIG. 1) also surround the region of interest of subject 100. FIG. 1 shows one embodiment of a cylindrical external coil which has a diameter sufficient to encompass the entire subject. Other geometries such as smaller cylinders specifically designed for imaging the head or an extremity can be used. Non-cylindrical external coils, such as surface coils may also be used. External coils 140 radiate radio frequency energy into subject 100 at predetermined times and with sufficient power at a predetermined frequency so as to nutate nuclear magnetic spins of subject 100 in a fashion well known to those skilled in the art. The nutation of the spins causes them to resonate at the Larmor frequency. The Larmor frequency for each spin is directly proportional to the strength of the magnetic field experienced by the spin. This field strength is the sum of the static magnetic field generated by magnet 125 and the local field generated by magnetic field gradient coil 130.

Device 150 is inserted into subject 100 by an operator 160. Device 150 may be a guide wire, a catheter, an endoscope, a laparoscope, a biopsy needle or similar device. This device contains at least two rf coils which detect MR signals generated in the subject responsive to the radio frequency field created by external coils 140. Since each rf coil is small, the region of sensitivity is also small. Consequently, the detected signals have Larmor frequencies which arise only from the strength of the magnetic field in the immediate vicinity of each coil. These detected signals are sent to an imaging and tracking unit 170 where they are analyzed. The position and orientation of device 150 is determined in imaging and tracking unit 170 and is displayed on a display means 180. In the preferred embodiment of the invention, the position and orientation of device 150 is displayed on display means 180 by superposition of a graphic symbol on a conventional MR image driven by a superposition means (shown as 174 in FIG. 6). In alternative embodiments of the invention, the graphic symbol representing device 150 is superimposed on diagnostic images obtained with other medical imaging systems shown as 172 in FIG. 1 such as a computed tomography (CT) scanner, a Positron Emission Tomography system or ultrasound scanner. Since CT scanners (and other X-ray imaging means), Positron Emission Tomography systems and Ultrasound scanners do not interfere with the steps of MR tracking, they may be operated during the steps of MR tracking. Alternatively, medical diagnostic images may be acquired with independent imaging means prior to initiating tracking and a symbol representing the location of the tracked device be superimposed on the previously acquired image. Other embodiments of the invention display the position of the device numerically or as a graphic symbol without reference to a diagnostic image.

Figure 2:
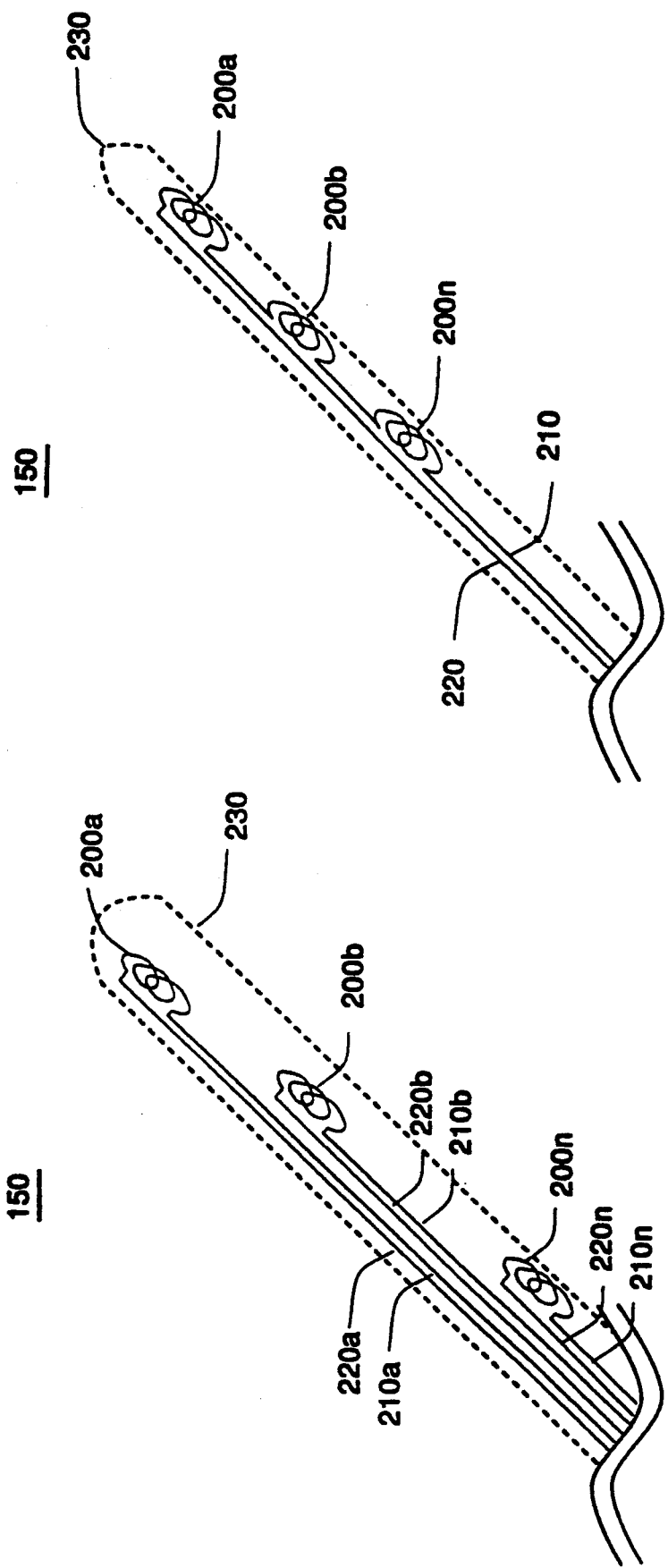
FIG. 2a is a schematic illustration showing incorporation of a plurality of rf coils into a medical device intended to be inserted into the body of a subject, with each coil having a unique connection to the MR system.
FIG. 2b is a schematic illustration showing incorporation of a plurality of rf coils into a medical device intended to be inserted into the body of a subject, with the coils having a common connection to the MR system.

Two embodiments of device 150 are shown in greater detail in FIGS. 2a and 2b. In the embodiment of FIG. 2a, a number of small rf coils 200a, 200b. . . 200n are electrically connected to the MR system via pairs of conductors 210a and 220a, 210b and 220b. . . 210n and 220n, respectively. In this embodiment, the signal from each rf coil may be processed independently. In the embodiment of FIG. 2b, rf coils 200a, 200b. . . 200n are connected in series and are connected to the AM system via a single pair of conductors. In this embodiment, the signals of all rf coils 200a, 200b. . . 200n are superimposed upon each other and must be extracted by frequency demultiplexing methods. Preferably, conductors have a coaxial structure. The rf coil and conductor pairs are encased in an outer shell 230 of device 150. The MR response signal arising from the tissue surrounding device 150 induces currents in coils 200a,200b. . . 200n.

Figure 3:
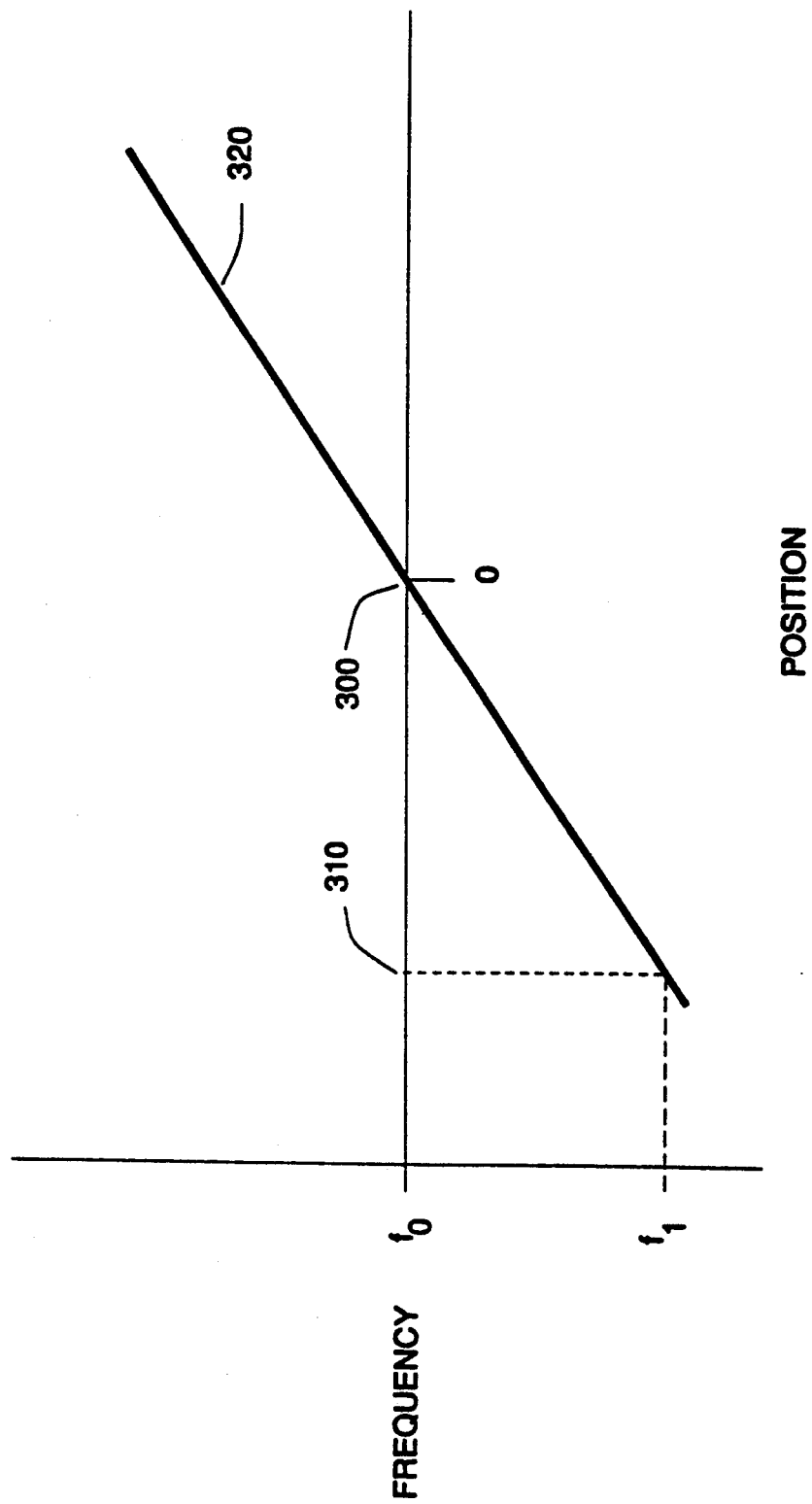
FIG. 3 is a graph of MR resonance frequency vs. position along a single axis in the presence of an applied magnetic field gradient.

Referring now to FIG. 3, the Larmor frequency of a spin is shown to be substantially proportional to its position when a magnetic field gradient is applied. A spin located at a center point 300 of the gradient coil (130 of FIG. 1) precesses at a Larmor frequency $f_0$. The Larmor frequency $f_0$ at point 300 is determined solely by the static magnetic field generated by magnet (125 of FIG. 1). A spin at a location 310 has a Larmor frequency $f_1$ determined by the sum of the static magnetic field and the additional magnetic field created at that location by magnetic field gradient coil (130 of FIG. 1). Since the gradient coil response 320 is substantially linear, the Larmor frequency of the spin is substantially proportional to position.

Figure 4:
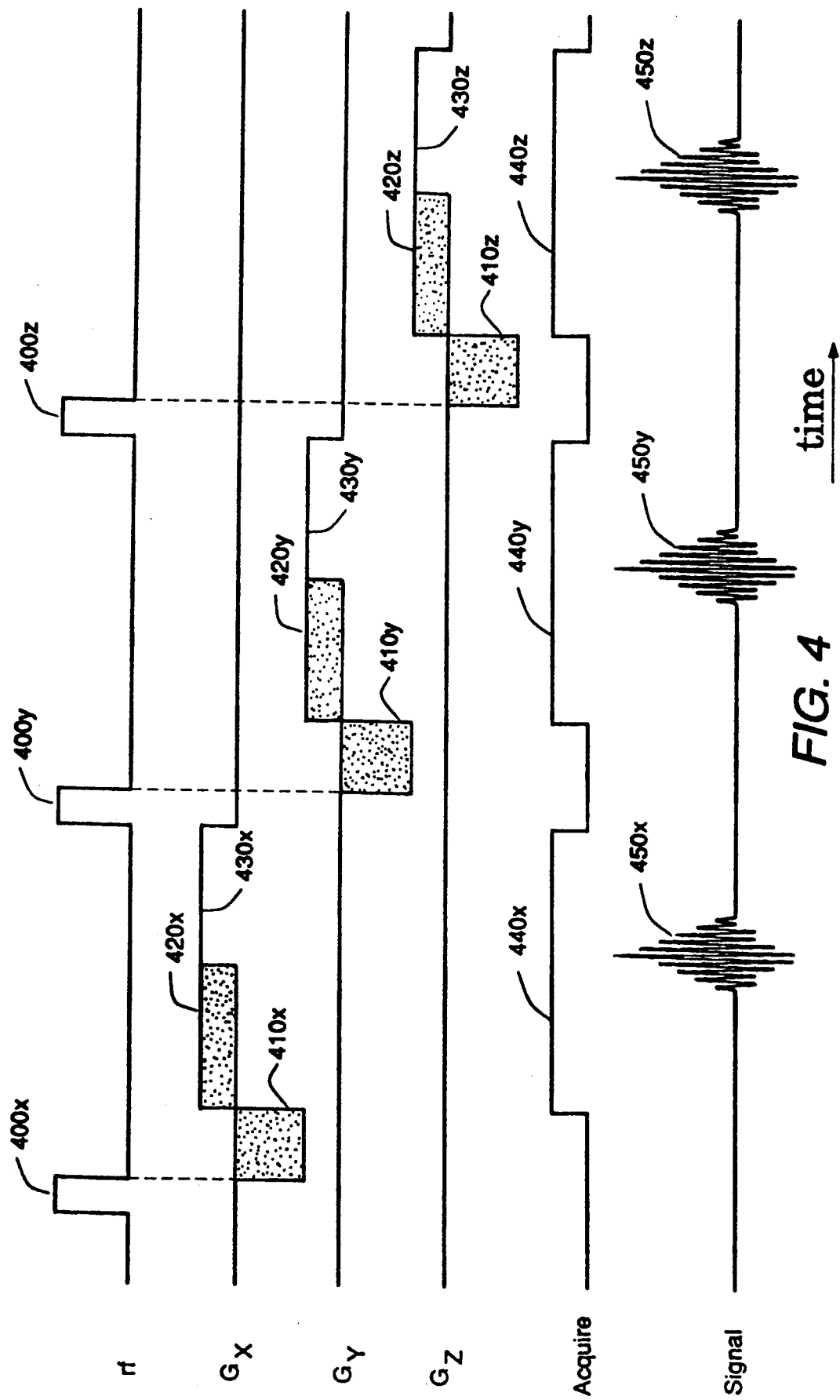
FIG. 4 is a timing diagram showing the relationships between rf pulses, magnetic field gradient pulses, data acquisition and detected signals in a first embodiment of the invention.

The MR response signals detected by rf coils 200a, 200b. . . 200n encased in device 150 as shown in FIGS. 2a and 2b are generated in response to the rf and magnetic field gradient pulses of the MR system. A presently preferred embodiment of the pulse timing is illustrated in FIG. 4. In this timing diagram, a first broadband rf pulse 400x excites aB spins of subject 100 within external coils 140 of FIG. 1. Shortly after first broadband rf pulse 400x a first magnetic field gradient pulse 410x is applied in a selected direction. Gradient pulse 410x dephases spin magnetization to a degree proportional to the position of the spin along the applied field gradient, (shown here to be in the X direction). Gradient pulse 410x is followed by a second magnetic field gradient pulse 420x having an opposite polarity to form a bilobed magnetic field gradient pulse. The product of the magnetic field gradient magnitude and duration of the gradient pulses (i.e., the areas of the regions shown in gray) are chosen to be substantially identical for the first and second gradient pulses. The amplitude of second magnetic field gradient pulse 420x is maintained effectively creating a third pulse 430x having an area substantially identical to that of second pulse 420x. Note that second 420x and third 430x gradient pulses in fact form a single pulse. This single pulse has been divided in two pulses solely for purposes of identification. At the end of the second gradient pulse all spins in subject 100 are substantially in phase. Third gradient pulse 430x causes additional dephasing of the MR signal.

During second gradient pulse 420x and third gradient pulse 430x, a data acquire signal 440x causes a first MR response signal 450x to be received from each coil 220. MR response signal 450x is digitized and stored in imaging and tracking unit 170 (FIG. 1). MR response signal 450x has a maximum substantially at the end of second gradient pulse 420x and a Larmor frequency which is substantially proportional to the position of device 150 (FIG. 1) along the direction of the applied magnetic field gradient. The frequency of MR response signal 450x is used to measure the position of each coil 220 in the device 150 (FIG. 1) in a first direction which is parallel to the direction of the applied field gradient, $G_x$.

A second broadband rf pulse 400y is applied immediately after acquisition of first MR response signal 450x. In a manner analogous to that used to determine the position of device 150 of FIG. 1 in the first direction, a fourth, fifth and sixth gradient pulse 410y, 420y, 430y, respectively, are applied in a second direction (here indicated to be in the Y direction) substantially orthogonal to the first direction. A data acquire signal 440y is generated during the period of the fifth and sixth gradient pulses 420y, 430y to cause a second AM response signal 450y to be digitized and stored in imaging and tracking unit 170 of FIG. 1. After detection of AM response signal 450y, a third broadband rf pulse 400z is applied and a seventh, eighth and ninth gradient pulse 410z, 420z, 430z, respectively, are applied in a third direction (shown here to be in the Z direction) substantially orthogonal to the first and second directions. A data acquire signal 440z is generated during the period of the eighth and ninth gradient pulses to cause a third MR response signal 450z to be digitized and stored in imaging and tracking unit 170 of FIG. 1.

After detection of third MR response signal 450z, the entire pulse sequence shown in FIG. 4 is repeated until tracking of the device is no longer desired. Alternatively, the entire pulse sequence shown in FIG. 4 is periodically interleaved with an imaging pulse sequence acquiring MR response signals from a conventional imaging rf coil to effect substantially simultaneous imaging of the subject and tracking of the device.

In another embodiment of this invention, the duration of third, sixth and ninth gradient pulses 430x, 430y, 430z, respectively, are extended to ensure that the signals are completely dephased before application of the next broadband rf pulse. This minimizes artifacts arising from spin phase coherence from multiple rf pulses. A second method of minimizing phase coherence is to use random phases in the MR system rf receiver and transmitter for each rf pulse.

In still another embodiment of this invention, the first, fourth and seventh gradient pulses 410x, 410y, 410z, respectively, are reduced in amplitude and/or duration without changing the remaining gradient pulses. This reduces the amount of dephasing each signal experiences prior to the data acquisition period and thus shifts the instant of .mum signal, but not its frequency. Reducing the duration of the first, fourth and seventh gradient pulses 410x, 410y, 410z, respectively, permits an advantageous reduction in the rf pulse interval.

Figure 5:
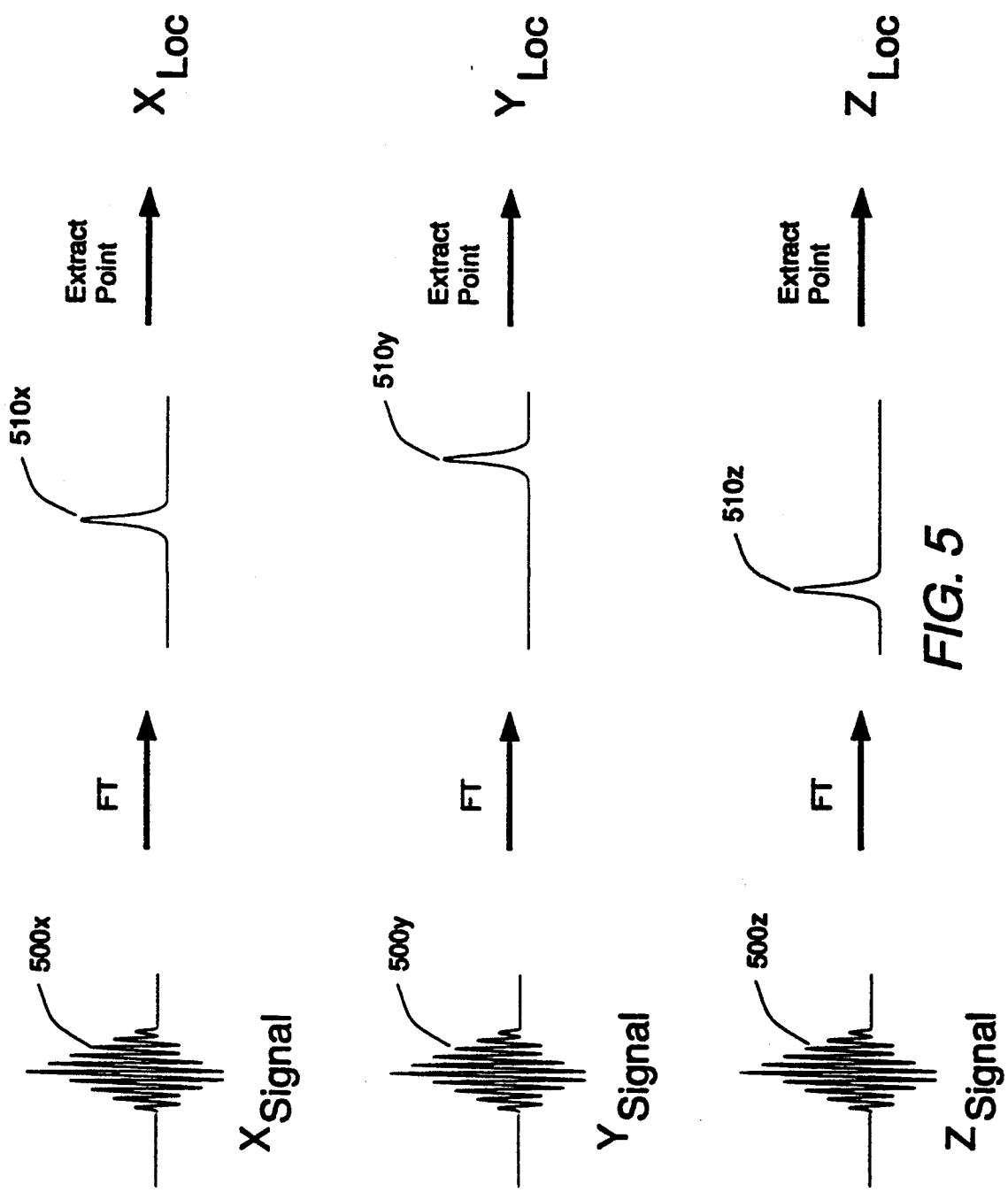
FIG. 5 is a diagram illustrating the steps required to determine, from an acquired MR response signal, the locations of two coils of a device.

FIG. 5 illustrates signals 600x, 600y, 600 z obtained from a number N of rf coils (200a, 200b...200n situated at different locations within device 150). Signals 600x, 600y, 600z are passed to a receiver and are Fourier transformed to yield frequency dependent data with N maxima. In the illustrated example of FIG. 5, N=2. One maximum 610x, 610y, 610z corresponds to the X, Y and Z position of a coil in the device, while the other maximum 620x, 620y, 620z corresponds to the X, Y and Z positions of another coil in the device.

It is also possible to selectively enable a predetermined one of the N coils at a chosen instant in time so that the position determination process represented in FIG. 5 is repeated N times for determining the position of a device.

In one embodiment of the invention the polarity of all gradient pulses ($G_x$, $G_y$, $G_z$) is reversed for each repetition of the sequence of FIG. 4. The acquired data is processed in the manner described in FIG. 5, but the positions calculated are averaged and displayed. Device positions obtained in this way are insensitive to differences in chemical shift which might occur as the device passes different types of tissue.

Figure 6:
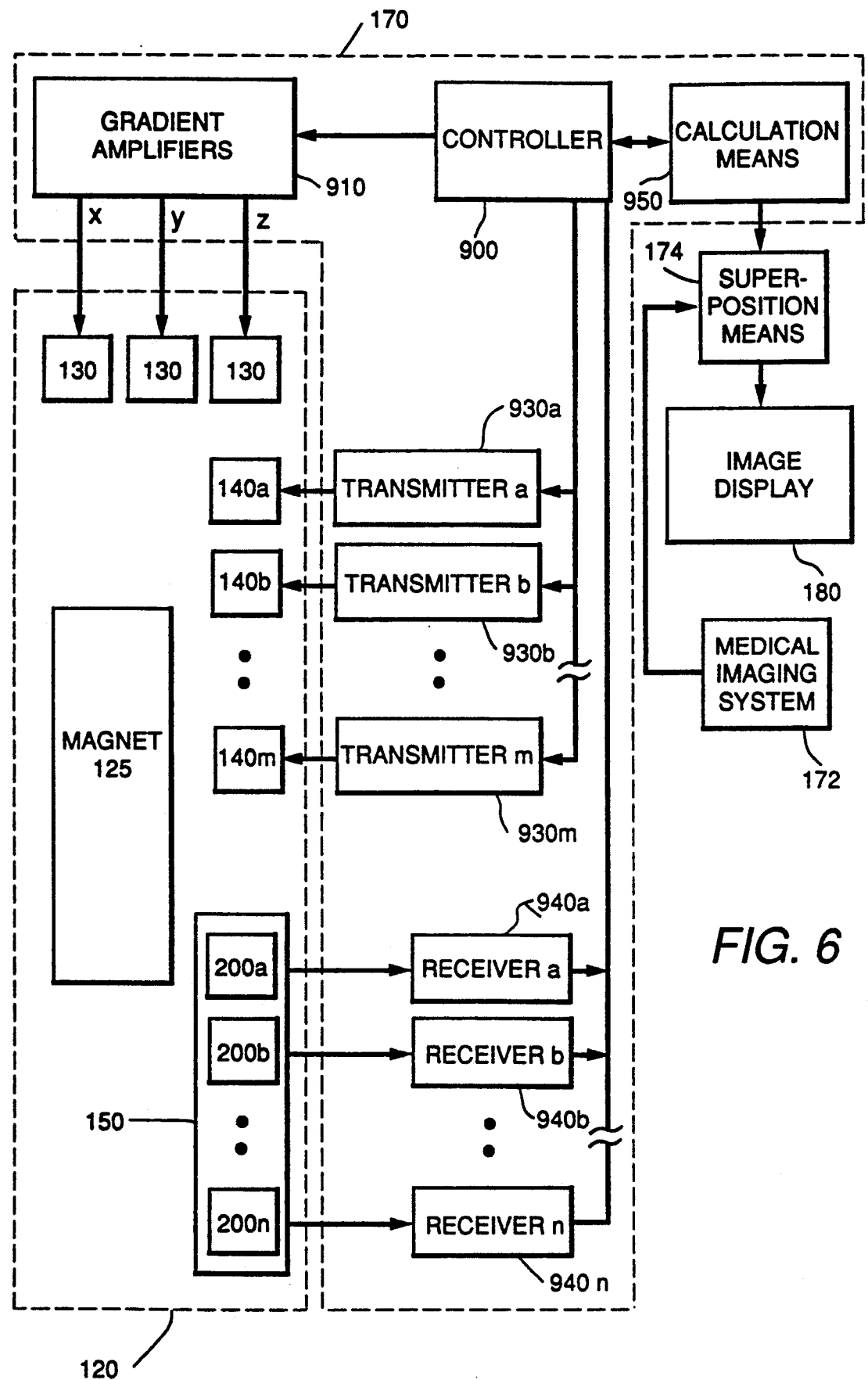
FIG. 6 is a block diagram of an MR imaging system suitable for device tracking using the present invention.

In FIG. 6, a block diagram of an MR system suitable for imaging and device tracking is illustrated. The system comprises a controller 900 which provides control signals to a set of magnetic field gradient amplifiers 910. These amplifiers drive magnetic field gradient coils 130 situated within the magnet enclosure 120. Gradient coils 130 are capable of generating magnetic field gradients in three mutually orthogonal directions. Controller 900 also generates signals which are supplied to transmitter means 930a, 930b. . .. 930m, causing them to generate rf pulses respectively at one or more predetermined frequencies and with suitable power to nutate selected spins within external coils 140a, 140b. . . 140m situated within the bore of magnet 125. MR signals are induced in rf coils 200a, 200b. . . 200n connected to receiver means 940a, 940b. . . 940n, respectively. The receiver means process the MR signal by amplifying, demodulating, filtering and digitizing. Controller 900 also collects the signals from receiver means 940a, 940b. . . 940n and propagates them to a calculation means 950 where they are processed. Calculation means 950 applies a Fourier transformation to the signals received from controller 900 to arrive at a plurality of positions for coils 200a, 200b. . . 200n. From these positions, the orientation of device 150 may be determined. The results calculated by calculation means 950 are displayed on an image display means 180.

Several embodiments of the present invention can be created using the MR system outlined in FIG. 6. The coils within device 150 are driven by one or more transmitters and the detected signals are propagated from device 150 to one or more receivers.

In the preferred embodiments of the invention, rf coils 200a, 200b. . . 200n situated within device 150 perform a receive function. Reciprocity between the transmit and receive coils exists, however, and tracking systems in which rf coils 200a, 200b. . . 200n situated in device 150 are used to transmit rf energy and external coils 140a, 140b. . . 140m are used to receive the MR response signal are possible.

While several presently preferred embodiments of the novel MR tracking system have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance (MR) tracking system comprising:
   a) an invasive device adapted to be inserted into a subject;
   b) static magnetic field means for applying a homogeneous magnetic field having substantially uniform amplitude over the subject;
   c) radiofrequency (rf) transmitter means adapted for transmitting rf energy into the subject of a selected duration, amplitude and frequency to cause nutation of a selected ensemble of spins within the subject;
   d) gradient means adapted for varying the amplitude of the magnetic field in at least one spatial dimension over the subject over time causing the selected ensemble of spins to emit an MR response signal;
   e) a plurality of rf coils each attached to the at least one invasive device, each rf coil adapted for detecting the MR response signal from the ensemble of spins in its vicinity;
   f) receiver means coupled to the rf coils adapted for processing the detected MR response signals from the selected ensemble of spins;
   g) calculation means adapted for calculating a location and orientation of the invasive device from the detected MR response signals;
   h) controller connected to the transmitter means, the receiver means, the calculation means and the gradient means, adapted for activating the rf transmitter means, the detection means, the calculation means and the gradient means according to a desired magnetic resonance sequence; and
   i) display means connected to the calculation means adapted for displaying the location of the invasive device to an operator.

2. The MR tracking system recited in claim 1, wherein the receiver means comprises:
   a) amplifying means adapted for amplifying the received MR response signal;
   b) filtering means for filtering the amplified MR response signal; and
   c) digitizing the amplified MR response signals.

3. The MR tracking system recited in claim 2, wherein the calculation means comprises means for determining the location and orientation of the at least one invasive device by calculating the location of each of the plurality of rf coils attached thereto.

4. The MR tracking system recited in claim 2, wherein the receiver means is selectively connectable to one rf coil at a selected instant for receiving the MR response signal detected by only the selected coil at the selected instant.

5. The MR tracking system recited in claim 1 further comprising:
   a) imaging means for acquiring a medical diagnostic image of the subject; and
   b) superposition means for superimposing a symbol on the medical diagnostic image at a position representing the calculated location of the invasive device.

6. The MR tracking system recited in claim 5, wherein the imaging means for acquiring a medical diagnostic image is an X-ray imaging means.

7. The MR tracking system recited in claim 5, wherein the means for acquiring a medical diagnostic image is an MR imaging system.

8. The MR tracking system recited in claim 5, wherein the means for acquiring a medical diagnostic image is an ultrasound imaging means.

9. The MR tracking system recited in claim 1, wherein the invasive device is one of the group consisting of a guide wire, a catheter, an endoscope, a laparoscope and a biopsy needle.

10. The MR tracking system recited in claim 1, wherein the invasive device is a surgical device.

11. The MR tracking system recited in claim 1, wherein the invasive device is a therapeutic device.

12. A method for tracing a location of at least one invasive device within a subject employing magnetic resonance (MR) comprising the steps of:
   a) applying a homogeneous magnetic field having substantially uniform amplitude over said subject;
   b) transmitting radiofrequency (rf) energy into said subject of a selected duration, amplitude and frequency to cause nutation of a selected ensemble of spins within said subject;
   c) varying the amplitude of the magnetic field in at least one spatial dimension over said subject over time causing the ensemble of spins within said subject to emit an MR response signal;
   d) detecting an MR response signal from a selected ensemble of spins from each of a plurality of rf coils attached to the at least one invasive device;
   e) processing the detected MR resonance signals;
   f) calculating a location and orientation of the at least one invasive device from the processed MR response signals; and
   g) displaying the location of said invasive device to a operator.

13. The method for tracking as recited in claim 12 further comprising the steps of:
   a) acquiring a medical diagnostic image of said subject; and
   b) superimposing a symbol on the medical diagnostic image at a position representing the calculated location of said invasive device.

14. The method for tracking as recited in claim 12, wherein the step of sensing the MR response signal occurs simultaneously with the step of varying the amplitude of the magnetic field.

15. The method for tracking as recited in claim 12, wherein the step of calculating a location of said invasive device further includes the step of performing a Fourier transformation on the MR response signals transforming time dependency to a frequency dependency, and mapping the frequency dependency to a number of locations.

16. A (MR) tracking system comprising:
a) an invasive device adapted to be inserted into a subject;
b) static magnetic field means for applying a homogeneous magnetic field having substantially uniform amplitude over the subject;
c) radiofrequency (rf) transmitter means attached to the at least one invasive device adapted for transmitting rf energy into the subject of a selected duration, amplitude and frequency to cause nutation of a selected ensemble of spins within the subject;
d) gradient means adapted for varying the amplitude of the magnetic field in at least one spatial dimension over the subject over time causing the selected ensemble of spins to emit an MR response signal;
e) a plurality of rf coils each adapted for detecting a different respective MR response signal from the ensemble of spins in its vicinity;
f) receiver means coupled to the rf coils adapted for processing the detected MR response signals from the selected ensemble of spins;
g) calculation means adapted for calculating a location and orientation of the invasive device from the detected MR response signals;
h) controller connected to the transmitter means, the receiver means, the calculation means and the gradient means, adapted for activating the rf transmitter means, the detection means, the calculation means and the gradient means according to a desired magnetic resonance sequence; and
i) display means connected to the calculation means adapted for displaying the location of the invasive device to an operator.

* * * * *